(12) United States Patent
Bels et al.

(10) Patent No.: US 10,295,554 B2
(45) Date of Patent: May 21, 2019

(54) BLOOD TESTING SYSTEM AND METHOD

(71) Applicant: C A Casyso GmbH, Basel (CH)

(72) Inventors: Kevin Bels, Munich (DE); Christian Brantl, Munich (DE); Johannes Wittmann, Munich (DE)

(73) Assignee: C A Casyso GmbH, Basel (CH)

( * ) Notice: Subject to any disclaimer, the term of this patent is extended or adjusted under 35 U.S.C. 154(b) by 688 days.

(21) Appl. No.: 14/754,300

(22) Filed: Jun. 29, 2015

(65) Prior Publication Data

US 2016/0377638 A1  Dec. 29, 2016

(51) Int. Cl.
*G01N 33/86* (2006.01)
*G01N 35/00* (2006.01)

(52) U.S. Cl.
CPC ....... *G01N 33/86* (2013.01); *G01N 35/00693* (2013.01)

(58) Field of Classification Search
CPC ........................................ G01N 33/86
USPC .............................. 422/73; 436/69
See application file for complete search history.

(56) References Cited

U.S. PATENT DOCUMENTS

| | | | |
|---|---|---|---|
| 2,555,937 A | 6/1951 | Rosenthal | |
| 2,995,425 A | 8/1961 | Hans | |
| 3,053,078 A * | 9/1962 | Jewett | G01N 11/14 73/53.01 |
| 3,714,815 A | 2/1973 | Hartert et al. | |
| 3,803,903 A | 4/1974 | Lin | |
| 3,903,903 A | 9/1975 | Matsumura | |
| 4,135,819 A * | 1/1979 | Schmid-Schonbein | G01N 15/05 356/39 |
| 4,148,216 A | 4/1979 | Do et al. | |
| 4,193,293 A | 3/1980 | Cavallari | |
| 4,202,204 A * | 5/1980 | Hartert | G01N 11/162 73/64.42 |
| D260,428 S | 8/1981 | Fekete | |
| 4,317,363 A * | 3/1982 | Shen | G01N 11/10 73/64.41 |

(Continued)

FOREIGN PATENT DOCUMENTS

| | | |
|---|---|---|
| CN | 1853104 | 10/2006 |
| CN | 101195112 | 6/2008 |

(Continued)

OTHER PUBLICATIONS

Anonymous: "Rotem® delta Whole Block Haemostasis System using Thromboelastometry US Operating Manual," [retrieved on Oct. 30, 2015]. Retrieved from the Internet: <URL:http://www.sfgh-poct.org/wp-content/uploads/2013/02/ROTEM-delta-US-Operating-Manual-Part-12.pdf>, 76 pages, Sep. 2012.

(Continued)

*Primary Examiner* — Arlen Soderquist
(74) *Attorney, Agent, or Firm* — Burns & Levinson, LLP

(57) ABSTRACT

Some embodiments of a blood coagulation testing system include an analyzer console device and a single-use components configured to releasably install into the console device. In some embodiments, the blood coagulation testing system can operate as an automated thromboelastometry system that is particularly useful, for example, at a point-of-care site. The systems can be configured with features such as individual actuation systems for each measurement module, and firmware for initial and ongoing calibration and error detection.

5 Claims, 10 Drawing Sheets

(56) References Cited

U.S. PATENT DOCUMENTS

| | | | |
|---|---|---|---|
| 4,319,194 A | 3/1982 | Cardinal | |
| 4,328,701 A * | 5/1982 | Mau-Tung | G01N 33/4905 73/54.26 |
| 4,341,111 A * | 7/1982 | Husar | G01N 33/4905 73/64.42 |
| 4,445,365 A * | 5/1984 | Selby | G01N 11/14 73/54.34 |
| 4,599,219 A | 7/1986 | Cooper | |
| 4,643,021 A * | 2/1987 | Mattout | G01N 33/4905 73/54.28 |
| 4,726,220 A | 2/1988 | Feier et al. | |
| 4,753,776 A | 6/1988 | Hillman et al. | |
| 4,756,884 A | 7/1988 | Hillman et al. | |
| 4,765,180 A | 8/1988 | Clifton | |
| 4,767,600 A | 8/1988 | Vicario | |
| 4,809,106 A * | 2/1989 | Inoue | G11B 5/5521 360/267.8 |
| D302,294 S | 7/1989 | Hillman | |
| 4,868,129 A | 9/1989 | Gibbons et al. | |
| 4,884,577 A * | 12/1989 | Merrill | A61B 5/02035 600/370 |
| D305,360 S | 1/1990 | Fechtner | |
| 4,936,674 A * | 6/1990 | Ikeda | G01N 15/0205 250/459.1 |
| 4,948,961 A | 8/1990 | Hillman et al. | |
| 4,956,089 A | 9/1990 | Hurst | |
| 4,963,498 A | 10/1990 | Hillman et al. | |
| 5,009,316 A | 4/1991 | Klein | |
| 5,016,469 A * | 5/1991 | Henderson | G01N 11/16 73/64.42 |
| 5,028,142 A | 7/1991 | Ostoich et al. | |
| 5,077,017 A | 12/1991 | Gorin et al. | |
| 5,104,813 A | 4/1992 | Besemer et al. | |
| D327,743 S | 7/1992 | Frenkel | |
| 5,164,598 A | 11/1992 | Hillman et al. | |
| 5,207,988 A | 5/1993 | Lucas | |
| 5,222,808 A | 6/1993 | Sugarman et al. | |
| 5,223,219 A | 6/1993 | Subramanian et al. | |
| 5,223,227 A | 6/1993 | Zuckerman | |
| 5,287,732 A | 2/1994 | Sekiguchi | |
| 5,302,348 A * | 4/1994 | Cusack | G01N 33/4905 422/534 |
| D347,067 S | 5/1994 | Shartle et al. | |
| 5,447,440 A | 9/1995 | Davis et al. | |
| 5,531,102 A | 7/1996 | Brookfield et al. | |
| 5,720,923 A * | 2/1998 | Haff | B01J 19/0046 422/129 |
| 5,777,212 A | 7/1998 | Sekiguchi et al. | |
| 5,777,215 A | 7/1998 | Calatzis et al. | |
| 5,788,928 A | 8/1998 | Carey | |
| 5,856,670 A * | 1/1999 | Rapkin | G01N 30/62 250/252.1 |
| 5,902,937 A | 5/1999 | Amrani et al. | |
| 6,012,712 A | 1/2000 | Bernstein | |
| 6,066,243 A | 5/2000 | Anderson et al. | |
| 6,200,532 B1 | 3/2001 | Wu et al. | |
| 6,225,126 B1 * | 5/2001 | Cohen | G01N 11/162 422/73 |
| 6,448,024 B1 | 9/2002 | Bruegger | |
| 6,537,819 B2 | 3/2003 | Cohen | |
| 6,573,104 B2 * | 6/2003 | Carr, Jr. | G01N 33/4905 422/49 |
| 6,613,286 B2 | 9/2003 | Braun et al. | |
| D481,133 S | 10/2003 | Blouin | |
| D482,454 S | 11/2003 | Gebrian | |
| 6,662,031 B1 | 12/2003 | Khalil et al. | |
| 6,699,718 B1 | 3/2004 | Bruegger | |
| 6,750,053 B1 | 6/2004 | Opalsky | |
| 6,838,055 B2 | 1/2005 | Sando et al. | |
| 6,942,836 B2 | 9/2005 | Freudenthal | |
| 6,951,127 B1 | 10/2005 | Bi | |
| 7,202,048 B2 * | 4/2007 | Carr, Jr. | C12Q 1/56 435/13 |
| 7,207,210 B2 * | 4/2007 | Moonay | G01N 11/14 73/54.28 |
| 7,399,637 B2 | 7/2008 | Wright et al. | |
| 7,412,877 B1 | 8/2008 | Bi | |
| 7,422,905 B2 | 9/2008 | Clague | |
| 7,491,175 B2 | 2/2009 | Ruether et al. | |
| 7,497,997 B2 | 3/2009 | Glezer et al. | |
| 7,524,670 B2 | 4/2009 | Cohen | |
| 7,595,169 B2 | 9/2009 | Swaim et al. | |
| 7,732,213 B2 | 6/2010 | Cohen et al. | |
| 7,745,223 B2 | 6/2010 | Schubert et al. | |
| 7,811,792 B2 | 10/2010 | Cohen | |
| 7,947,505 B2 | 5/2011 | Kawasaki et al. | |
| D645,973 S | 9/2011 | Hoenes | |
| 8,110,392 B2 | 2/2012 | Battrell et al. | |
| 8,168,442 B2 | 5/2012 | Petersen | |
| 8,322,195 B2 * | 12/2012 | Glauner | G01N 33/4905 73/54.33 |
| 8,383,045 B2 | 2/2013 | Schubert et al. | |
| 8,448,499 B2 | 5/2013 | Schubert et al. | |
| 8,857,244 B2 | 10/2014 | Schubert et al. | |
| 9,006,149 B2 * | 4/2015 | Garcia-Cardena | C12M 35/04 506/10 |
| 9,110,084 B2 | 8/2015 | Schubert et al. | |
| D737,993 S | 9/2015 | Tan | |
| 9,086,423 B2 | 9/2015 | Schubert et al. | |
| 9,272,280 B2 | 3/2016 | Viola | |
| 9,285,377 B2 | 3/2016 | Schubert | |
| 9,428,790 B2 * | 8/2016 | De Laat | C12Q 1/56 |
| D777,343 S | 1/2017 | Gorin et al. | |
| 9,546,981 B2 * | 1/2017 | Wu | G01N 27/74 |
| 2001/0053552 A1 * | 12/2001 | Cohen | G01N 11/162 436/69 |
| 2002/0081741 A1 | 6/2002 | Braun, Sr. | |
| 2002/0168294 A1 * | 11/2002 | Carr, Jr. | G01N 33/4905 422/73 |
| 2003/0073244 A1 | 4/2003 | Cohen et al. | |
| 2003/0107812 A1 * | 6/2003 | Chen | G02B 7/005 359/579 |
| 2003/0154772 A1 * | 8/2003 | Jackson | G01N 11/14 73/54.28 |
| 2003/0199428 A1 * | 10/2003 | Carr, Jr. | C12Q 1/56 435/13 |
| 2004/0131500 A1 | 7/2004 | Chow | |
| 2005/0202566 A1 * | 9/2005 | Frojmovic | G01N 15/05 436/63 |
| 2005/0233466 A1 | 10/2005 | Wright | |
| 2006/0075805 A1 * | 4/2006 | Moonay | G01N 11/14 73/54.28 |
| 2007/0059840 A1 | 3/2007 | Cohen et al. | |
| 2008/0026476 A1 | 1/2008 | Howell | |
| 2008/0160500 A1 | 7/2008 | Fuller | |
| 2008/0227217 A1 | 9/2008 | Yamamoto et al. | |
| 2008/0251383 A1 | 10/2008 | Sobek | |
| 2008/0297169 A1 | 12/2008 | Greenquist | |
| 2009/0130645 A1 | 5/2009 | Schubert et al. | |
| 2010/0139375 A1 * | 6/2010 | Johns | G01N 11/08 73/54.24 |
| 2010/0154520 A1 | 6/2010 | Schubert et al. | |
| 2010/0170327 A1 * | 7/2010 | Glauner | G01N 33/4905 73/54.41 |
| 2010/0184201 A1 | 7/2010 | Schubert et al. | |
| 2010/0323916 A1 * | 12/2010 | Garcia-Cardena | C12M 23/12 506/10 |
| 2011/0237913 A1 | 9/2011 | Schubert et al. | |
| 2012/0294761 A1 | 11/2012 | Viola | |
| 2013/0323847 A1 | 12/2013 | Schubert et al. | |
| 2014/0004613 A1 | 1/2014 | Goldstein | |
| 2014/0271409 A1 | 9/2014 | Knight | |
| 2015/0024473 A1 * | 1/2015 | Wu | G01N 27/74 435/287.1 |
| 2015/0118691 A1 * | 4/2015 | De Laat | C12Q 1/56 435/7.4 |
| 2016/0091415 A1 | 3/2016 | Furukawa | |
| 2016/0091483 A1 | 3/2016 | McCluskey | |
| 2016/0091514 A1 | 3/2016 | Gorin et al. | |
| 2016/0091515 A1 | 3/2016 | Gorin et al. | |
| 2016/0091516 A1 | 3/2016 | Gorin | |

(56) References Cited

U.S. PATENT DOCUMENTS

| | | | |
|---|---|---|---|
| 2016/0091517 A1 | 3/2016 | Gorin | |
| 2016/0161510 A1* | 6/2016 | Gorlinger | G16H 50/20 435/13 |
| 2016/0195557 A1 | 7/2016 | Schubert | |
| 2016/0313357 A1 | 10/2016 | Viola | |

FOREIGN PATENT DOCUMENTS

| | | |
|---|---|---|
| DE | 2740932 | 11/1978 |
| DE | 10135569 | 2/2003 |
| DE | 202014002289 | 9/2014 |
| EP | 0404456 | 12/1990 |
| EP | 1367392 | 12/2003 |
| EP | 1394546 | 3/2004 |
| EP | 1627725 | 2/2006 |
| EP | 1884778 | 2/2008 |
| EP | 1901065 | 3/2008 |
| EP | 2208996 B1 | 9/2010 |
| EP | 2202517 B1 | 8/2012 |
| GB | 1353481 * | 5/1974 |
| GB | 2257256 | 1/1993 |
| JP | 1971004947 A1 | 11/1971 |
| JP | 1987140047 A1 | 6/1987 |
| JP | 1991031764 A1 | 2/1991 |
| JP | 1997-159596 | 6/1997 |
| JP | 09-507580 | 7/1997 |
| JP | H09507580 A | 7/1997 |
| JP | 2006-053142 | 2/2006 |
| JP | 2012515340 A1 | 7/2012 |
| JP | 2015045642 A1 | 3/2015 |
| WO | WO 1989/006803 | 7/1989 |
| WO | 96/12954 | 5/1996 |
| WO | WO 2002/50535 | 6/2002 |
| WO | WO 2002/063273 | 8/2002 |
| WO | WO 2005/106467 | 11/2005 |
| WO | WO 2006/091650 | 8/2006 |
| WO | WO 2006/126290 | 11/2006 |
| WO | WO 2007/047961 | 4/2007 |
| WO | WO2008075181 A2 | 6/2008 |
| WO | WO 2010072620 | 7/2010 |
| WO | WO 2008/093216 | 8/2011 |
| WO | WO 2011/117017 | 9/2011 |
| WO | WO 2014/103744 | 7/2014 |
| WO | WO 2014/115478 | 7/2014 |

OTHER PUBLICATIONS

Lang et al., "Evaluation of the new device ROTEM platelet" [retrieved on Oct. 28, 2015]. Retrieved from the Internet: <URL: https://www.rotem.de/wp-content/uploads/2014/09/Lang-et-al-2014.pdf>, Jan. 1, 2014.

International Search Report and Written Opinion for PCT/IB2016/053860, dated Sep. 19, 2016, 12 pages.

"HealthPACT, ""Rotational thromboelastometry (ROTEM)—targeted therapy for coagulation management in patients with massive bleeding,"" Health PolicyAdvisory Committee on Technology. Retrieved from the Internet: <URL: https://www.health.qld.gov.au/healthpact/docs/briefs/WP024.pdf>, 30 pages, Nov. 2012".

European Search Report in European Application No. 15174565.0, dated Nov. 17, 2015, 9 pages.

Chinese Office Action for Application No. 200980151858.5 dated May 21, 2013, 16 pages.

Chinese Office Action for Application No. 200980151858.5, dated Feb. 14, 2014, 4 pages.

European Extended Search Report for Application No. 13167983.9, dated Nov. 6, 2013, 3 pages.

European Office Action for Application No. 08172769.5, dated Jun. 1, 2011, 12 pages.

European Office Action for Application No. 12179576.9, dated May 22, 2013, 10 pages.

European Office Action for Application No. 13163014.7, dated Mar. 24, 2014, 12 pages.

European Office Action for Application No. 13167979.7, dated Nov. 15, 2016, 8 pages.

European Search Report and Opinion for Application No. 15187347.8, dated Jun. 1, 2016, 16 pages.

International Preliminary Report on Patentability for PCT/EP2009/067181, dated Jun. 29, 2011, 9 pages.

International Search Report and Written Opinion for Application No. PCT/EP2009/067181, dated Mar. 22, 2010, 12 pages.

Japanese Notification of Refusal for Application No. 2011-541392, dated Jun. 14, 2013, 4 pages.

Japanese Notification of Refusal for Application No. 2014-165975, dated Jul. 17, 2015, 8 pages.

Korean Office Action for Application No. 1020117017187, dated Mar. 28, 2016, 11 pages.

Korean Office Action for Application No. 1020167029191, dated Nov. 17, 2016, 5 pages.

Notification of Reasons for Refusal for Application No. 2015-132034, dated Jul. 29, 2016, 4 pages.

ROTEM®, "Targeted therapy for coagulation management in patients with massive bleeding," https://www.health.qld.gov.au/_data/assets/pdf_file/0023/427145/wp024.pdf, Nov. 2012, 30 pages, [brochure].

International Search Report and Written Opinion for International Application No. PCT/US2016/064790, dated Feb. 15, 2017, 17 pages.

International Search Report and Written Opinion for International Application No. PCT/US2016/064797, dated Feb. 15, 2017, 16 pages.

International Search Report and Written Opinion for International Application No. PCT/US2016/064806, dated Feb. 15, 2017, 18 pages.

International Search Report and Written Opinion for International Application No. PCT/US2016/64800, dated Feb. 16, 2017, 14 pages.

Office Action in corresponding European Application No. EP15174565.0 dated Oct. 19, 2017.

Calatzis et al., "Strategies to Assess Individual Susceptibility to abciximab Therapy Using a New Functional Assay," *Annals of Hematology*, (Berlin, DE) vol. 76, No. Suppl 1, p. A61, XP009097526, 1998.

Chakroun et al., "The influence of fibrin polymerization and platelet-mediated contractile forces on citrated whole blood thromboelastography profile," *Thromb Haemost.*, 95(5):822-828, May 2006.

Greilich et al., "Near-site monitoring of the antiplatelet drug abciximab using the Hemodyne analyzer and modified thrombelastograph," *J Cardiothorac Vasc Anesth.*, 13(1):58-64, Feb. 1999.

Hartert, "Blood Coagulation Studies with Thromboelastography—A New Research Method," *Klin Wochenschrift*, 26:577-583, Oct. 1948 [English translation].

Kawasaki et al., "The effects of vasoactive agents, platelet agonists and anticoagulation on thromboelastography," *Acta Anaesthesiol Scand.*, 51(9):1237-1244, Oct. 2007.

Khurana et al., "Monitoring platelet glycoprotein IIb/IIIa-fibrin interaction with tissue factor-activated thromboelastography," *J Lab Clin Med.*, 130(4):401-411, Oct. 1997.

Nield et al., "MRI-based blood oxygen saturation measurements in infants and children with congenital heart disease," *Pediatr Radiol.*, 32(7):518-522. Epub Apr. 16, 2002.

Nielsen et al., "Evaluation of the contribution of platelets to clot strength by thromboelastography in rabbits: the role of tissue factor and cytochalasin D," *Anesth Analg.*, 91(1):35-39, Jul. 2000.

Noon et al., "Reduction of blood trauma in roller pumps for long-term perfusion" *World J Surg.*, 9(1):65-71, Feb. 1985.

Novotny et al., "Platelets secrete a coagulation inhibitor functionally and antigenically similar to the lipoprotein associated coagulation inhibitor," *Blood*, 72(6):2020-2025, Dec. 1988.

Prisco and Paniccia, "Point-of-Care Testing of Hemostasis in Cardiac Surgery", *Thromb J.*, 1(1):1, May 6, 2003.

Rodzynek et al., "The transfer test: a new screening procedure for thrombotic diseases," *J Surg Res.*, 35(3):227-233, Sep. 1983.

ROTEM® "When Minutes Count to Stop the Bleeding," Pentapharm GmbH, www.rotem.de, 6 pages, Jun. 2007. [brochure].

ROTEM® delta, "Targeted therapy stops the bleeding," 6 pages, Jan. 6, 2014, [brochure].

(56) References Cited

OTHER PUBLICATIONS

ROTEM® delta, "Whole Blood Haemostasis System using Thromboelastomerty Operating Manual," 164 pages, Nov. 17, 2014 [brochure].
Rugeri et al., "Diagnosis of early coagulation abnormalities in trauma patients by rotation thromboelastography," *J Thromb Haemost.*, 5(2):289-295, Epub Nov. 16, 2006.
Salooja and Perry, "Thromboelastography," *Blood Coagul Fibrinolysis*, 12(5):327-37, Jul. 2001.
Shore-Lesserson et al., "Thromboelastography-guided transfusion algorithm reduces transfusions in complex cardiac surgery," *Anesth Analg.*, 88(2):312-319, Feb. 1999.
Soria et al., "Fibrin stabilizing factor (F XIII) and collagen polymerization," *Experientia*, 31(11):1355-1357, Nov. 15, 1975.
Spannagl et al., "Point-of-Care Analysis of the Homeostatic System," *Laboratoriumsmedizin*, (Kirchheim, DE), 26(1-2):68-76, Feb. 2002.
Srinivasa et al., "Thromboelastography: Where Is It and Where Is It Heading?" *Int'l Anesthesiology Clinics*, 39(1):35-49, Winter 2001.
Tanaka et al., "Thrombin generation assay and viscoelastic coagulation monitors demonstrate differences in the mode of thrombin inhibition between unfractionated heparin and bivalirudin," *Anesth Analg.*, 105(4):933-939, Oct. 2007.
Extended European Search Report (EESR) for European Application No. 18210029.7, dated Jan. 30, 2019.
Office Action issued in counterpart Japanese Application No. 2018-037666, dated Feb. 22, 2019 and English translation thereof (8 total pages).
Office Action issued in counterpart Canadian Application No. 2,990,573, dated Jan. 25, 2019 (5 total pages).

\* cited by examiner

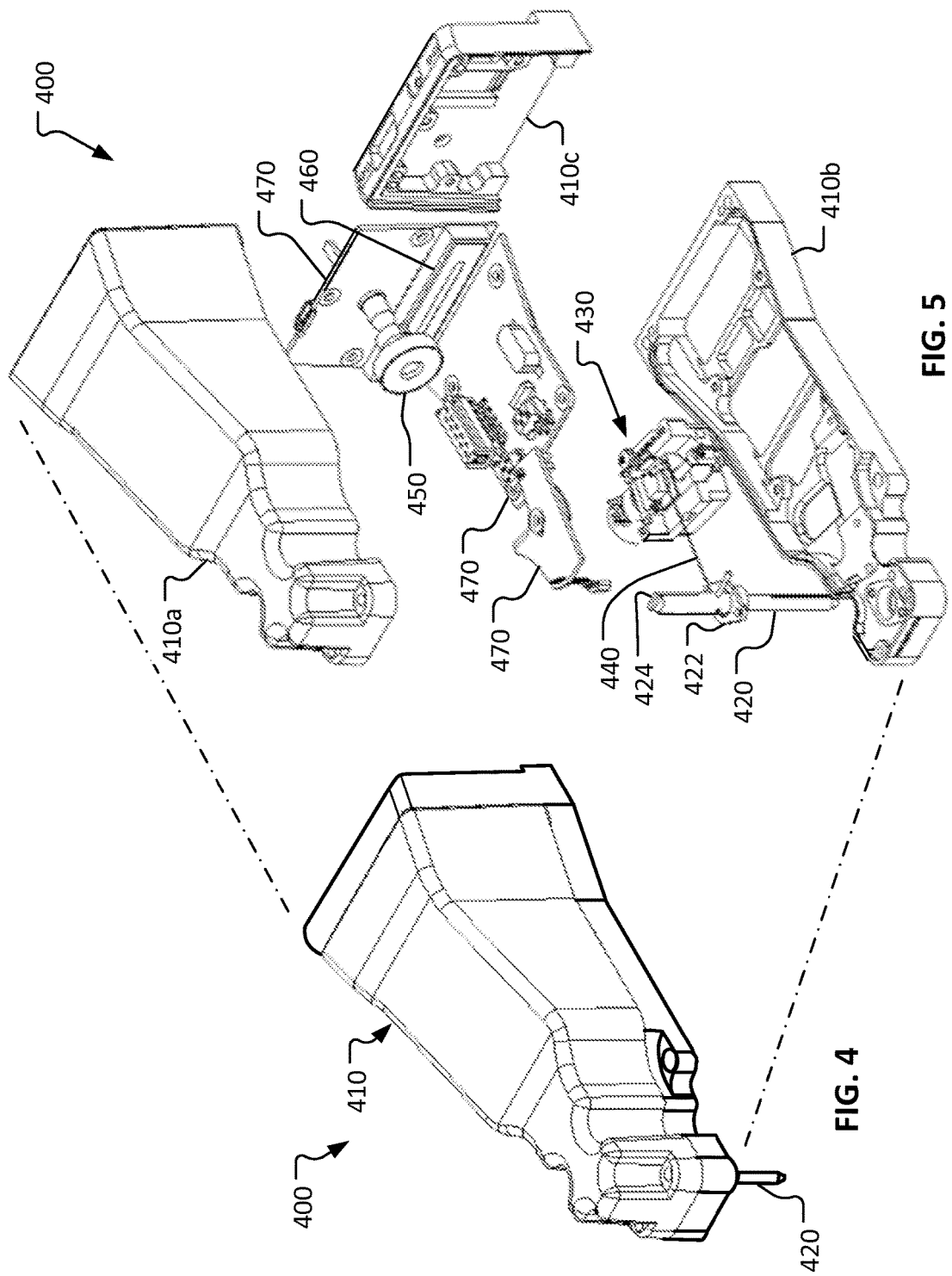

BLOOD TESTING SYSTEM AND METHOD

TECHNICAL FIELD

This document relates to systems and methods for testing characteristics of a blood sample, such as an automated thromboelastometry system for point-of-care whole blood coagulation analysis.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of blood to form an adequate clot and to determine the blood clot's stability. Common laboratory tests such as thrombocyte counts or the determination of fibrin concentration provide information on whether the tested component is available in sufficient amount, but some of those tests might not determine whether the tested component works properly under physiological conditions. Other laboratory tests work on blood plasma, which may impose additional preparation steps and additional time beyond what is preferred, for example, in the point-of-care context (e.g., in a surgical theater during a surgical operation).

Another group of tests to assess the potential of blood to form an adequate clot is known as "viscoelastic methods." In at least some viscoelastic methods, the blood clot firmness (or other parameters dependent thereon) is determined over a period of time, for example, from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction. To isolate and test particular functions of thrombocytes, fibrinogen, and other factors in a blood sample, reagent compounds can be mixed with the blood sample to activate or inhibit certain components in the blood sample.

SUMMARY

Some embodiments of a system for testing characteristics of a blood sample (which, as used herein, should be understood to include blood or derivatives of blood such as plasma) include a control console configured for testing a blood sample to provide a point-of-care whole blood coagulation analysis. For example, the system can serve as an automated thromboelastometry system for providing detailed and prompt results of blood coagulation characteristics in response to receiving one or more samples of blood that have been mixed with various types of reagents.

In some embodiments, the thromboelastometry system includes a reusable analyzer console and one or more single-use components configured to mate with the console. In one example, to operate the thromboelastometry system, a user is prompted by a user interface of the analyzer console to initiate a number of blood and reagent transfer and mixing operations. Thereafter, the analyzer console automatically performs (without requiring further user interaction with the analyzer console or the blood sample) the testing and displays the results on a graphical display using qualitative graphical representations and quantitative parameters. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

In one implementation, a control console for measuring coagulation characteristics of a blood sample includes: (i) a control unit housing, (ii) a user interface coupled to the control unit housing for displaying coagulation characteristics of a blood sample, and (iii) a plurality of individual thromboelastometry measurement modules housed in the control unit housing. Each measurement module of the plurality of individual thromboelastometry measurement modules includes a shaft configured to receive a probe for testing the blood sample using a probe and cup arrangement. Each individual measurement module of the plurality of individual thromboelastometry measurement modules includes a dedicated actuation unit that drives rotation of a respective shaft of the individual measurement module independently from rotation of shafts of all other individual measurement modules of the plurality of individual thromboelastometry measurement modules.

Such a control console for measuring coagulation characteristics of a blood sample may optionally include one or more of the following features. In some embodiments, the actuation unit comprises a stepper motor. The stepper motor may optionally include a threaded driveshaft. In various embodiments, the actuation unit also includes a slider unit. The slider unit may have a threaded collar that is threadably engaged with the threaded drive shaft of the motor such that the motor can drive the slider unit to translate linearly. In particular embodiments, the actuation unit also includes a spring wire. In some such embodiments, a linear translation of the slider unit may cause a pivoting of the shaft because of the spring wire extending between the slider unit and the shaft.

In various embodiments of the control console for measuring coagulation characteristics of a blood sample, the actuation unit further comprises a magnet that attracts the spring wire to the slider unit. The spring wire may be magnetically attracted to a curved surface of the slider unit. Optionally, the actuation unit may include a sensor that is configured to detect a position of the slider unit. In some embodiments, the sensor includes a Hall effect sensor. In various embodiments, the actuation unit may include one or more end-of-travel sensors that are configured to detect travel limits of the slider unit. The control console may also include one or more vibration sensors housed in the control unit housing. In some embodiments, each individual measurement module of the plurality of individual thromboelastometry measurement modules includes one or more vibration sensors.

In particular embodiments of the control console for measuring coagulation characteristics of a blood sample, each individual measurement module of the plurality of individual thromboelastometry measurement modules includes an evaluation unit for evaluating a charge-coupled device (CCD) component. In some embodiments, the evaluation unit may be configured to: (i) receive brightness distribution data from the CCD, (ii) generate CCD calibration data based on the brightness distribution data, and (iii) compare the CCD calibration data to real-time-measured CCD brightness distribution data. In some embodiments, each individual measurement module of the plurality of individual thromboelastometry measurement modules may further include a heater configured to heat a cup of the probe and cup arrangement.

In another implementation, a method for evaluating a CCD component of a thromboelastometry analysis system is performed by one or more processors of the thromboelastometry analysis system, or by one or more processors of an individual AD-module. The method includes receiving brightness distribution data from the CCD, generating CCD calibration data (wherein the CCD calibration data is generated based on the brightness distribution data from the CCD), and comparing (while the thromboelastometry analysis system is performing a thromboelastometry analysis) the CCD calibration data to real-time-measured CCD brightness distribution data. In some embodiments, the brightness distribution data from the CCD represents individual brightness data from a plurality of individual pixels of the CCD.

Such a method for evaluating a CCD component of a thromboelastometry analysis system performed by one or more processors of the thromboelastometry analysis system or one or more processors of an individual AD-module may optionally include one or more of the follow features. In some embodiments, the method further includes determining, a position of a falling or rising edge of the brightness distribution data from the CCD.

In another implementation, a method of controlling accuracy of a thromboelastometry analysis system is performed by one or more processors of the thromboelastometry analysis system, or by one or more processors of an individual AD-module. The method includes receiving vibration data indicative of a detected level of vibration of the thromboelastometry analysis system, comparing the received vibration data to a threshold limit value, and generating a vibration error indication in response to the received vibration data being greater than the threshold limit value.

Such a method of controlling accuracy of a thromboelastometry analysis system may optionally include one or more of the following features. In some embodiments, the method also includes receiving, at one or more processors of the thromboelastometry analysis system, positional indication data indicative of a detected position of a slider unit in relation to an actuation unit of the thromboelastometry analysis system. In particular embodiments, the method also includes comparing, by the one or more processors of the thromboelastometry analysis system, the received positional indication data to one or more threshold limit values. In various embodiments, the method also includes generating, by the one or more processors of the thromboelastometry analysis system and based on the comparison of the received positional indication data to the one or more threshold limit values, a position error indication in response to the received positional indication data being greater than the one or more threshold limit values.

In another implementations, a method of controlling accuracy of a thromboelastometry analysis system is performed by one or more processors of the thromboelastometry analysis system, or by one or more processors of an individual AD-module. The method includes receiving positional indication data indicative of a detected position of a slider unit in relation to a actuation unit of the thromboelastometry analysis system, comparing the received positional indication data to one or more threshold limit values, and generating (based on the comparison of the received positional indication data to the one or more threshold limit values) a position error indication in response to the received positional indication data being greater than the one or more threshold limit values.

Such a method of controlling accuracy of a thromboelastometry analysis system may optionally include one or more of the following features. In some embodiments, the positional indication data includes one or more signals from one or more end-of-travel sensors that indicate whether the slider unit is positioned at a targeted travel limit position. In particular embodiments, the positional indication data includes one or more signals from one or more sensors that indicate a real-time position of the slider unit as the slider unit linearly translates back and forth along a linear path.

Some or all of the embodiments described herein may provide one or more of the following advantages. First, some embodiments of a thromboelastometry system described herein are configured with independent actuation units for individual modules or channels of multiple testing and measurement channels. For example, in some embodiments the thromboelastometry system includes four modules or channels, each of which has an independent actuation unit. Accordingly, the actuation of each testing and measurement module can be controlled independently of the other testing and measurement module. In addition, the use of independent actuation units for each module of multiple testing and measurement modules provides a modular design that affords advantages for the performance of maintenance on the system in some scenarios.

Second, the actuation units of some embodiments of the thromboelastometry system are driven using a rotary actuator that is positionally controllable (e.g., a stepper motor coupled to a programmable stepper motor control system, or another type of suitable rotary actuator with encoder feedback coupled to a control system). The use of positionally controllable actuators (e.g., motors) advantageously allows for programmable actuation patterns. In addition, in some embodiments stepper motors allow for greater precision of rotary thromboelastometry system actuation, as compared to some other types of motors. Further, in some embodiments the stepper motors provide enhanced isolation from some external error influences, such as vibration.

Third, some embodiments of the thromboelastometry system are configured with firmware for self-evaluation and calibration of the CCD (charge-coupled device) portion of the thromboelastometry detection system. Accordingly, measurement inaccuracies can be reduced or eliminated in some cases. In some such embodiments, the functionality of each individual pixel of the CCD is verified prior to operation of thromboelastometry tests. In result, the consistency of the performance of the thromboelastometry system is enhanced.

Fourth, some embodiments of the thromboelastometry system are configured with additional firmware for supervising and evaluating functional aspects of the rotary thromboelastometry actuation and detection systems. For example, in some embodiments vibrations that might distort the measurement signals are detected and used to manage the thromboelastometry system. Further, in some embodiments sensors are included that detect the movement and end-of-travel positions of the rotary thromboelastometry actuation systems. These systems for supervising and evaluating functional aspects of the rotary thromboelastometry actuation and detection systems provide a robust measurement system and facilitate enhanced measurement quality (e.g., enhanced accuracy and/or precision of the thromboelastometry measurements).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a perspective view of an example actuation and detection module (also referred to herein as an "AD-module" or "ADM") for an individual thromboelastometry measurement channel of the thromboelastometry system of FIG. 1.

FIG. 5 is a perspective exploded view of the example AD-module of FIG. 4.

Like reference symbols in the various drawings indicate like elements.

DETAILED DESCRIPTION OF ILLUSTRATIVE EMBODIMENTS

Figure 1:
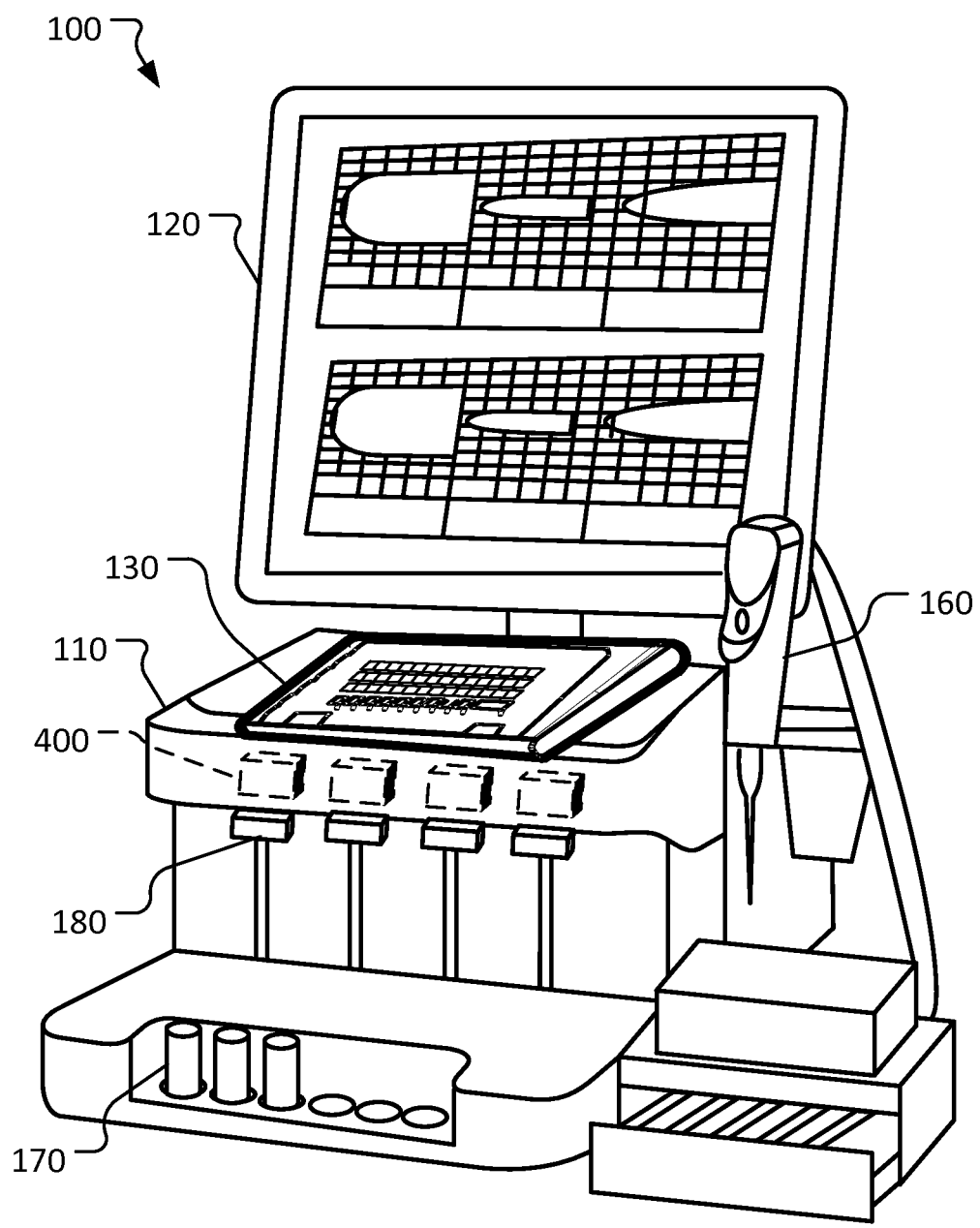
FIG. 1 is a perspective view of an example thromboelastometry system, in accordance with some embodiments.

Referring to FIG. 1, some embodiments of an example blood testing system 100 include a blood analyzer console 110 along with a graphical user interface 120 that is coupled with the analyzer console 110. In the depicted embodiment, the blood testing system 100 is a thromboelastometry system that is configured to determine a number of blood coagulation characteristics of a blood sample. One example of such a thromboelastometry system 100 is the ROTEM® delta Thromboelastometry system available from Tem International GmbH headquartered in Munich, Germany. Thromboelastometry and thromboelastography are based on the measurement of the elasticity of blood by continuous graphic logging of the firmness of a blood clot during clot formation (e.g., pertaining to coagulation factors and inhibitors, platelets and fibrin) and subsequent fibrinolysis.

The example thromboelastometry system 100 performs in vitro blood diagnostics, and is particularly advantageous at a point-of-care site (e.g., in a surgical theater while a patient is undergoing or preparing for surgery, or the like). Additionally, the thromboelastometry system 100 can be used as a whole blood coagulation analysis system in a laboratory setting. The thromboelastometry system 100 provides a quantitative and qualitative indication of the coagulation state of a blood sample.

Figure 2:
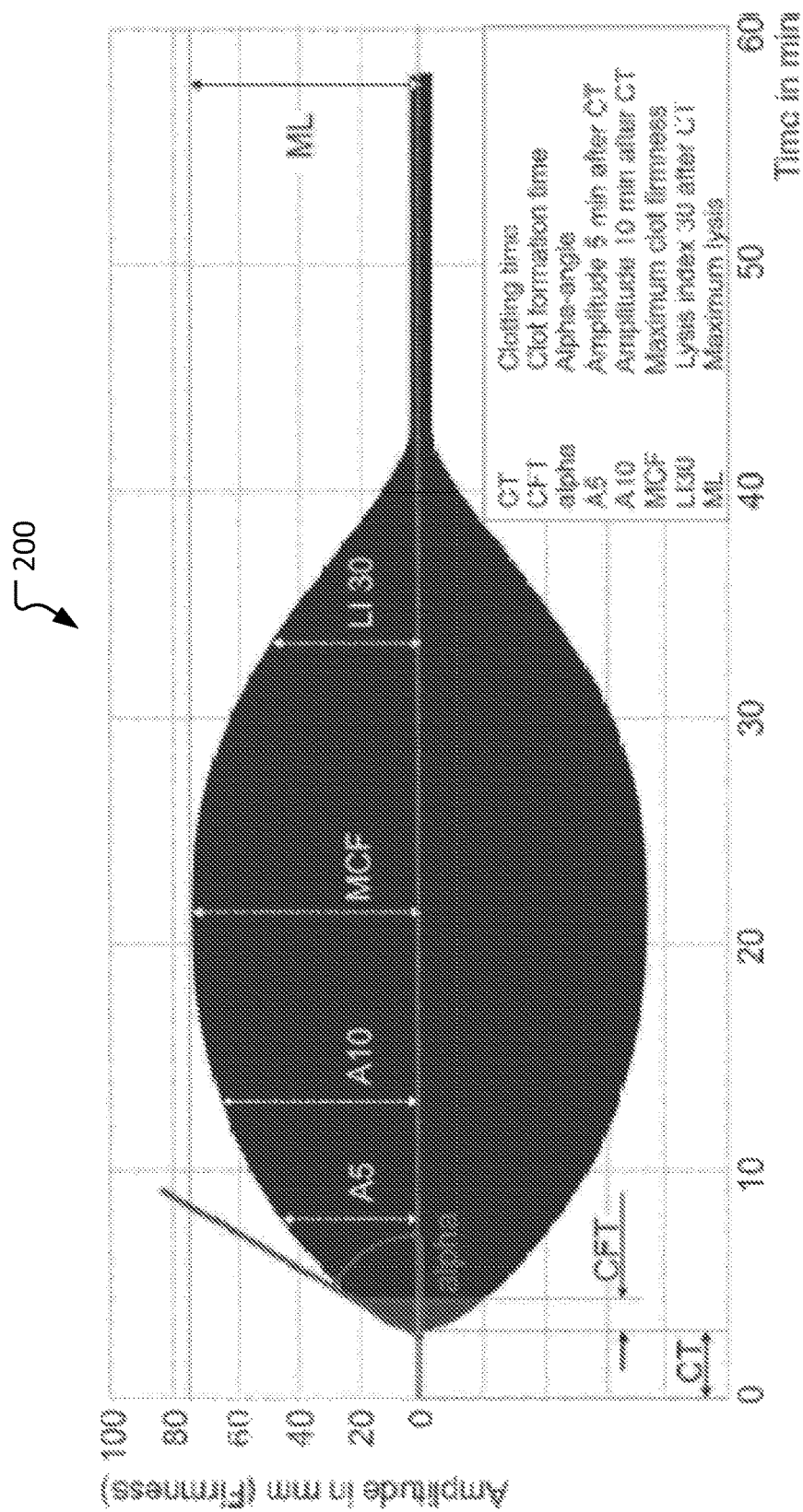
FIG. 2 is an example of a graphic that quantifies the firmness of a blood clot during clot formation, as calculated and displayed by the thromboelastometry system of FIG. 1.

In some embodiments, a graphical presentation displayed on the graphical user interface 120 reflects the various blood diagnostic results (e.g., one or more plots, such as those sometimes refer to as a TEMogram, numeric data or measurements, or a combination thereof), which may describe the interaction between components like coagulation factors and inhibitors, fibrinogen, thrombocytes, and the fibrinolysis system. For example, referring also to FIG. 2, in some embodiments the graphical user interface 120 provides a continuous graphic logging of the firmness of a blood clot during clot formation as a graphical presentation 200. FIG. 2 is an example of a graphic 200 that quantifies the firmness of a blood clot during clot formation, as calculated and displayed by the thromboelastometry system 100 during the performance of an assay, for example. In some embodiments, multiple such graphical presentations 200 pertaining to the firmness of a blood clot during clot formation are concurrently displayed on the graphical user interface 120.

Still referring to FIG. 1, in some embodiments the analyzer console 110 houses the hardware devices and sub-systems that control the operations of the thromboelastometry system 100. For example, the analyzer console 110 houses one or more processors and memory devices that can store an operating system and other executable instructions. In some embodiments, the executable instructions, when executed by the one or more processors, are configured to cause the system 100 to perform operations such as analyzing of the blood test result data indicative of the blood coagulation characteristics, and outputting via the user interface 120.

In some embodiments, the analyzer console 110 also houses various internal sub-systems, includes various electronic connection receptacles (not shown), and includes a cartridge port (not shown). The various electronic connection receptacles can include network and device connectors such as, but not limited to, one or more USB ports, Ethernet ports (e.g., RJ45), VG A connectors, Sub-D9 connectors (RS232), and the like. Such connection receptacles can be located on the rear of the analyzer console 110, or at other convenient locations on the analyzer console 110. For example, in some embodiments one or more USB ports may be located on or near the front of the analyzer console 110. A USB port, so located, may provide user convenience for recording data onto a memory stick, for example. In some embodiments, the thromboelastometry system 100 is configured to operate using wireless communication modalities such as, but not limited to, Wi-Fi, Bluetooth, NFC, RF, IR, and the like.

Still referring to FIG. 1, in some embodiments, the graphical user interface 120 is also used to convey graphical and/or textual user instructions to assist a user during the preparation of a blood sample for testing by the thromboelastometry system 100. Optionally, the graphical user interface 120 is coupled to the analyzer console 110 and is a touchscreen display whereby the user can, for example, input information and make menu item selections. In some embodiments, the graphical user interface 120 is rigidly attached to the analyzer console 110. In particular embodiments, the graphical user interface 120 is pivotable and/or is otherwise positionally adjustable or removable in relation to the analyzer console 110.

The blood testing system 100 may also include a keyboard 130, and/or other types of user input devices such as a mouse, touchpad, trackball, and the like. In some embodiments, the thromboelastometry system 100 also includes an external barcode reader. Such an external barcode reader can facilitate convenient one-dimensional or two-dimensional barcode entry of data such as, but not limited to, blood sample data, user identification, patient identification, normal values, and the like. Alternatively or additionally, the thromboelastometry system 100 can be equipped with a reader configured to read near-field communication tags, RFID tags, or the like. In some embodiments, a computer data network (e.g., intranet, internet, LAN, etc.) may be used to allow for remote devices to receive and/or input information from the thromboelastometry system 100.

The depicted thromboelastometry system 100 also includes an electronic system pipette 160. Using the system pipette 160, a user can conveniently dispense volumetrically measured amounts of liquids (such as blood or reagents) during the process of preparing a blood sample prior to testing. In some embodiments, the system pipette 160 is a semi-automatic, software controlled device. For example, in some embodiments the system pipette 160 automatically extracts a targeted amount of liquid from one container, and then the user can dispense the targeted amount of liquid into another container.

In some embodiments, operation of the blood testing system 100 includes the use one or more reagents 170 that are mixed with a blood sample prior to performance of thromboelastometry. For example, the reagents 170 can comprise compounds such as, but not limited to, $CaCl_2$, ellagic acid/phospholipids, tissue factor, heparinase, polybrene, cytochalasin D, tranexamic acid, and the like, and combinations thereof. In some embodiments, the thromboelastometry system 100 will provide user instructions (e.g., via the graphical user interface 120) to mix particular reagents 170 with the blood sample using the system pipette 160.

The thromboelastometry analyzer console 110 also includes one or more individual thromboelastometry measurement stations 180 (which may also be referred herein to as "channels" or "measurement modules"). The depicted embodiment of thromboelastometry system 100 includes four individual thromboelastometry measurement stations 180 (i.e., four channels or four measurement modules).

As described further below, each thromboelastometry measurement station 180 includes a cup holder into which a user places a sample cup containing blood and reagents in preparation for thromboelastometry testing. In some embodiments, the cup holders are equipped with a heating system so that the samples can be warmed to and held approximately at body temperature (e.g., 37+/−1.0° C.).

As described further below, in some embodiments each thromboelastometry measurement station 180 includes a pin or probe that can be removably positioned within the cup containing the sample to be tested. A clearance space exists between the probe and cup. In some embodiments, the shaft and probe is oscillated or otherwise rotated, back and forth, by about less than 10° (in both rotational directions), and preferably about 3° to about 6° (in both rotational directions). In some embodiments, such oscillations of the shaft and probe can be equal in magnitude in both rotational directions. The oscillations are measured, and as the blood/reagent mixture begins to become firmer because of thrombolysis, the oscillations are reduced. The measurements, by the thromboelastometry measurement station 180, of such oscillations over a period of time thereby generates thromboelastometry results.

Figure 3:
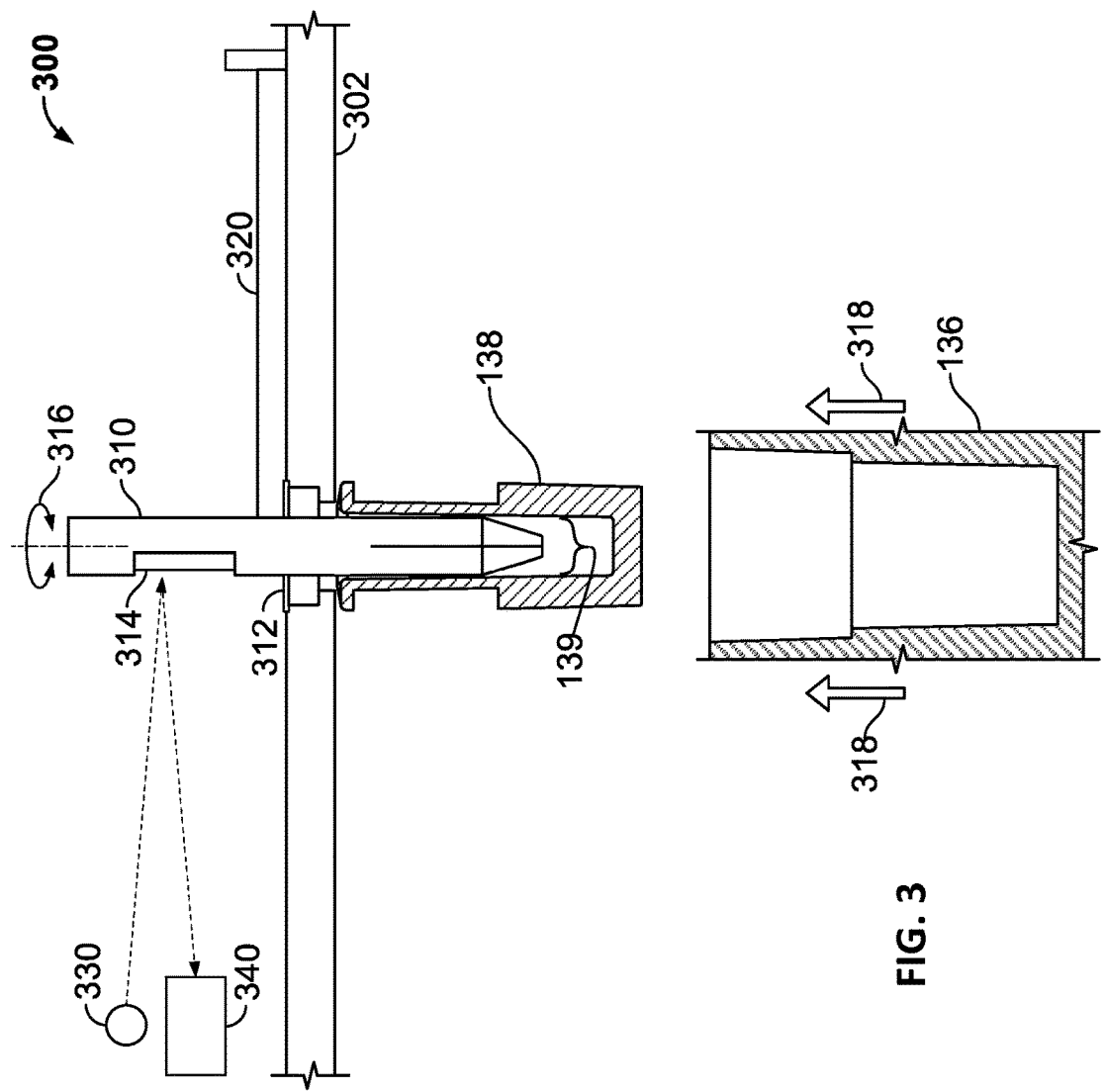
FIG. 3 is a schematic diagram depicting an example rotary thromboelastometry detection system portion of the thromboelastometry system of FIG. 1.

Referring also to FIG. 3, an example rotary thromboelastometry actuation and detection system 300 that can be present in each thromboelastometry measurement station 180 (measurement module) is schematically depicted. In some implementations, a shaft 310 of the actuation and detection system 300 can engage with a single-use probe 138 to perform rotary thromboelastometry on a blood sample contained in a single-use cup 136. In FIG. 3, the probe 138 and the cup 136 are shown in longitudinal cross-sections to allow for enhanced visibility and understanding of the example rotary thromboelastometry actuation and detection system 300 as a whole. In some embodiments, the probe 138 has an outer diameter of about 6 mm, and the cup 136 has an inner diameter of about 8 mm. However, the dimensions of the cup 136 and the probe 138 can be made suitably larger or smaller.

In this particular embodiment, the schematically depicted example rotary thromboelastometry actuation and detection system 300 includes a baseplate 302, a shaft 310, a bearing 312, a mirror 314, a counterforce spring wire 320, a light source 330, and a detector 340 (e.g., a charge-coupled device (CCD) or the like). The single-use cup 136 can be raised (e.g., by a user), as represented by arrows 318, such that a tip portion of the shaft 310 enters the bore 139 of the probe 138 to become releasably coupled with the probe 138. The bearing 312 is engaged with the baseplate 302 and the shaft 310 to facilitate rotational movement of the shaft 310 in relation to the baseplate 302. The spring wire 320 is coupled to the shaft 310 and an induced motion of the spring wire 320 (as driven by a motor described further below) can induce the shaft 310 to oscillate back and forth by less than 10° (in both rotational directions), and preferably about 3° to about 6° (in both rotational directions) as represented by arrow 316. The mirror 314 is coupled to the shaft 310. The light source 330 is configured to project light towards the mirror 314, and light can be reflected from the mirror 314 towards the detector 340 (in a direction that is dependent on the rotational orientation of the shaft 310). Accordingly, the motion of the probe 138 is detected by an optical detection system (e.g., the detector 340). It should be understood that other configurations of the rotary thromboelastometry actuation and detection system 300 are also envisioned within the scope of this disclosure.

As the blood in the cup 136 begins to coagulate, the motion amplitude of the shaft 310 starts to decrease (as detected by the reflection of the light beam from mirror 314 towards the detector 340). During coagulation, the blood's fibrin backbone (together with platelets) creates a mechanical elastic linkage between the surfaces of the cup 136 and the probe 138. A proceeding coagulation process induced by adding one or more of the aforementioned activating factors (e.g., reagents) can thus be observed and quantified.

The detected motion data from the detector 340 is analyzed by an algorithm running on the analyzer console 110 to process and determine the thromboelastometry results. This system facilitates various thromboelastometry parameters such as, but not limited to, clotting time, clot formation time, alpha angle, amplitude, maximum clot firmness, lysis onset time, lysis time, lysis index (%), and maximum lysis (%). In this way, various deficiencies of a patient's hemostatic status can be revealed and can be interpreted for proper medical intervention. At the end of the test process, the cup 136 can be lowered to uncouple the shaft 310 from the probe 138.

Still referring to FIG. 1, the analyzer console 110 can house one or more rotary thromboelastometry actuation and detection modules (AD-modules) 400 corresponding (e.g., one-to-one) with the one or more individual thromboelastometry measurement stations 180. Such rotary thromboelastometry AD-modules 400 can operate, for example, like the example rotary thromboelastometry actuation and detection system 300 described above in reference to FIG. 3.

Referring to FIG. 4, an individual rotary thromboelastometry AD-module 400, broadly speaking, can include a housing 410 and a shaft 420. The shaft 420 can be configured to releasably couple with a single-use probe (e.g., probe 138 of FIG. 3) for the performance of thromboelastometry and/or thromboelastography as described above. That is, the shaft 420 can be rotationally oscillated back and forth, for example by less than 10° (in both rotational directions), and preferably about 3° to about 6° (in both rotational directions) as described above.

Referring also to FIG. 5, an exploded view of the rotary thromboelastometry AD-module 400 provides a greater visibility of the primary components of the AD-module 400. For example, the rotary thromboelastometry AD-module 400 includes the housing 410 (including three housing portions 410a, 410b, and 410c), the shaft 420, an actuation unit 430, a spring wire 440, an LED 450, a CCD 460, and a printed circuit board (PCB) assembly 470.

In some embodiments, the housing 410 includes a cover 410a, a base plate 410b, and a back-cover 410c. The housing 410 contains the other components of the AD-module 400, except for a portion of the shaft 420 which protrudes beyond the base plate 410b so that the shaft 420 can engage with a single-use probe. Accordingly, in some embodiments the AD-module 400 is a discrete module that can be removed and replaced as a unit.

The rotary thromboelastometry AD-module 400 also includes the shaft 420. In the depicted embodiment, the shaft 420 includes a bearing 422 and a mirror 424. When the AD-module 400 is assembled, the bearing 422 is rigidly coupled with the base plate 410b. Hence, the shaft 420 can freely rotate in relation to the base plate 410b. The mirror 424, which is affixed to the shaft 420, is configured to reflect light from the LED 450 towards the CCD 460. As the shaft 420 oscillates during rotary thromboelastometry testing, the direction of the mirror 424 also oscillates correspondingly (because the mirror 424 is affixed to the shaft 420). Therefore, during rotary thromboelastometry testing, light from the LED 450 will be reflected off of the mirror 424 (and towards the CCD 460) at changing angles as the shaft 420 oscillates.

The rotary thromboelastometry AD-module 400 also includes the actuation unit 430. The actuation unit 430 (which will be described in more detail in reference to FIG. 6 below) provides the motive force that causes the shaft 420 to rotationally oscillate.

In the depicted embodiment, a spring wire 440 provides the linkage between the actuation unit 430 and the shaft 420. In other words, the actuation unit 430 drives the spring wire 440, and the spring wire 440 transmits the driving force from the actuation unit 430 to the shaft 420.

The rotary thromboelastometry AD-module 400 also includes the LED 450. In some embodiments, the LED 450 is rigidly mounted to the PCB assembly 470, and the PCB assembly is rigidly mounted to the housing 410. The LED 450 emits light that is steadily directed toward the mirror 424. In some embodiments, one or more lenses are used in conjunction with the LED 450.

Light from the LED 450 reflects off of the mirror 424 in the direction of the CCD 460. The CCD 460 includes multiple pixels that are arranged along the face of the CCD 460 (e.g., arranged generally linearly). Accordingly, the light reflected from the mirror 424 scans across the face of the CCD 460 as the shaft 420 pivots. By detecting the positions of the particular pixels of the CCD 460 that receive the LED light, the angular position and other characteristics pertaining to the angular rotation of the shaft 420 can be determined. In some embodiments, other types of light detectors (other than a CCD type of detector) are used instead of, or in addition to the CCD 460.

The rotary thromboelastometry AD-module 400 also includes the PCB assembly 470. The PCB assembly 470 includes electronic devices and circuitry that are used for the operation of the rotary thromboelastometry AD-module 400. In particular embodiments, the PCB assembly 470 (including executable code stored therein) comprises an evaluation unit configured for receiving brightness distribution data from the CCD, generating CCD calibration data based on the brightness distribution data, and comparing the CCD calibration data to real-time-measured CCD calibration data. In some embodiments, the PCB assembly 470 includes a microprocessor, motor driver, fuses, integrated circuits, and the like. The PCB assembly 470 can also include one or more types of sensors such as, but not limited to, vibration sensors, accelerometers, Hall-effect sensors, end-of-travel detectors, proximity sensors, optical sensors, microswitches, and the like.

Figure 6:
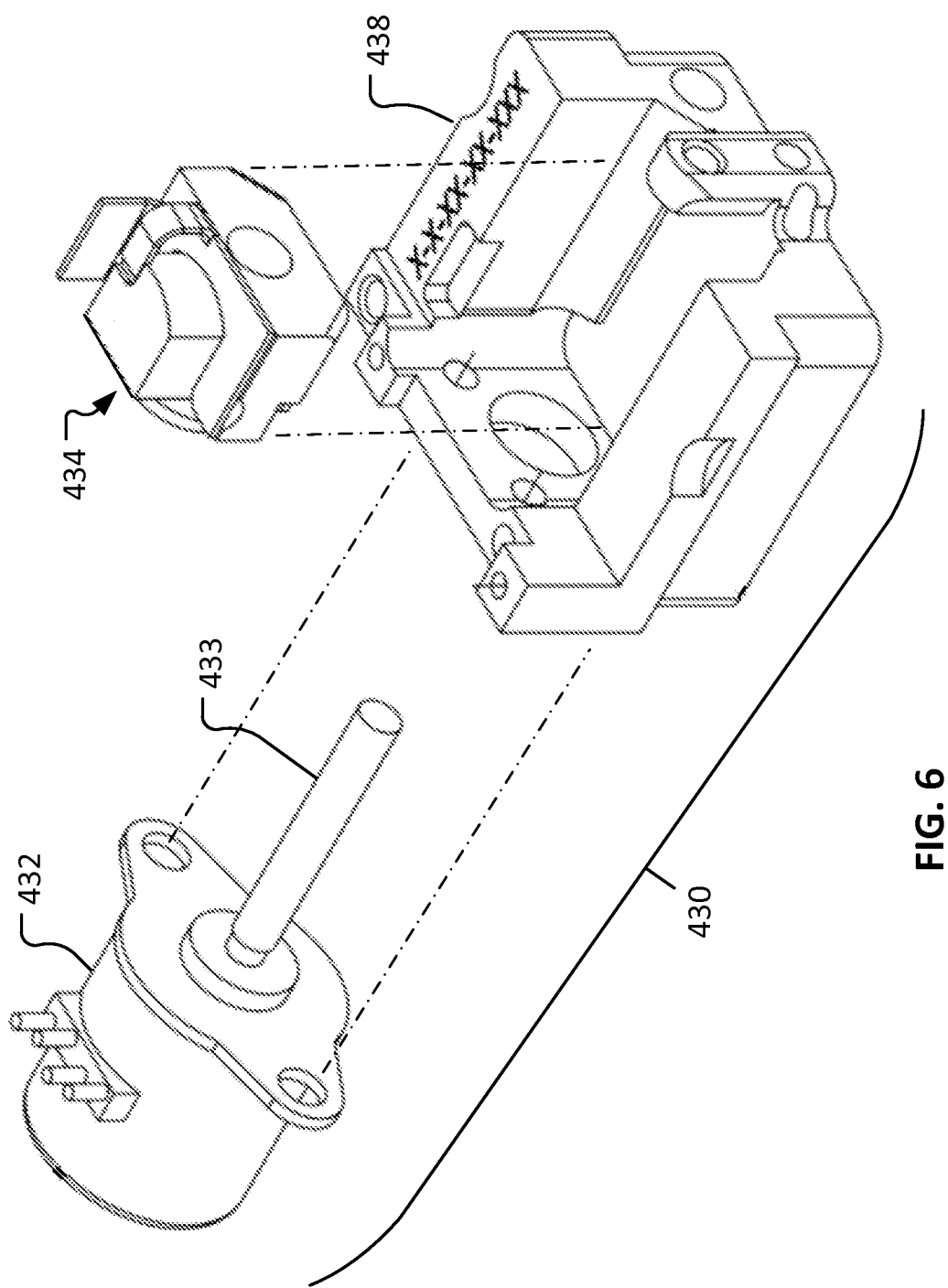
FIG. 6 is a perspective exploded view of an actuation unit of the example AD-module of FIG. 4.

Referring to FIG. 6, an example actuation unit 430 of the rotary thromboelastometry AD-module 400 is shown in an exploded perspective view for greater visibility of the actuation unit's components. In the depicted embodiment, the actuation unit 430 includes a motor 432, a slider unit 434, and a slider guidance member 438. The motor 432 is mounted to the slider guidance member 438. The slider unit 434 is slidably engaged with the slider guidance member 438. The motor 432 is engaged with the slider unit 434 so that the motor 432 can provide a motive force to the slider unit 434, as described further below.

The example actuation unit 430 is designed so as to provide a number of operational advantages. For example, as will become more evident from the description below, the actuation unit 430 is compact, lightweight, resistant to external vibrations, mechanically precise, electronically instrumented, highly controllable, repeatably positionable, durable, and so on.

In some embodiments, the motor 432 is a stepper motor. Accordingly, in some such embodiments the motor 432 can be programmed and controlled to rotate and operate in a prescribed fashion. That is, in some embodiments the motor 432 can be programmed to operate in accord with selected parameters—including parameters such as, but not limited to, rotational speed, number of revolutions, acceleration, deceleration, direction, and the like. Such factors can be programmed into the memory of the rotary thromboelastometry AD-module 400 or the analyzer console 110. Therefore, various actuation curves for the motor 432 can be readily selected and/or adjusted as desired. In some implementations, all rotary thromboelastometry AD-modules 400 are programmed to operate using the same actuation curve. In other implementations, one or more rotary thromboelastometry AD-module 400 are programmed to operate using a different actuation curve in comparison to one or more other rotary thromboelastometry AD-modules 400.

The motor 432 includes a drive shaft 433. In some embodiments, the drive shaft 433 is a lead screw. The external threads of the lead screw can be threadably engaged with an internally-threaded portion of the slider unit 434. In some such embodiments, the drive shaft 433 is finely-threaded lead screw to facilitate precise and smooth control of the slider unit 434. When the drive shaft 433 and the slider unit 434 are threadably engaged, a rotation of the motor 432 will result in a linear translation of the slider unit 434. That is, as the drive shaft 433 of the motor 432 rotates, the slider unit 434 will slidably translate within the slider guidance member 438. When the motor 432 reverses its direction of rotation (e.g., clockwise versus counter-clockwise), the linear direction of the slider unit 434 in relation to the slider guidance member 438 will be reversed correspondingly.

Figure 7:
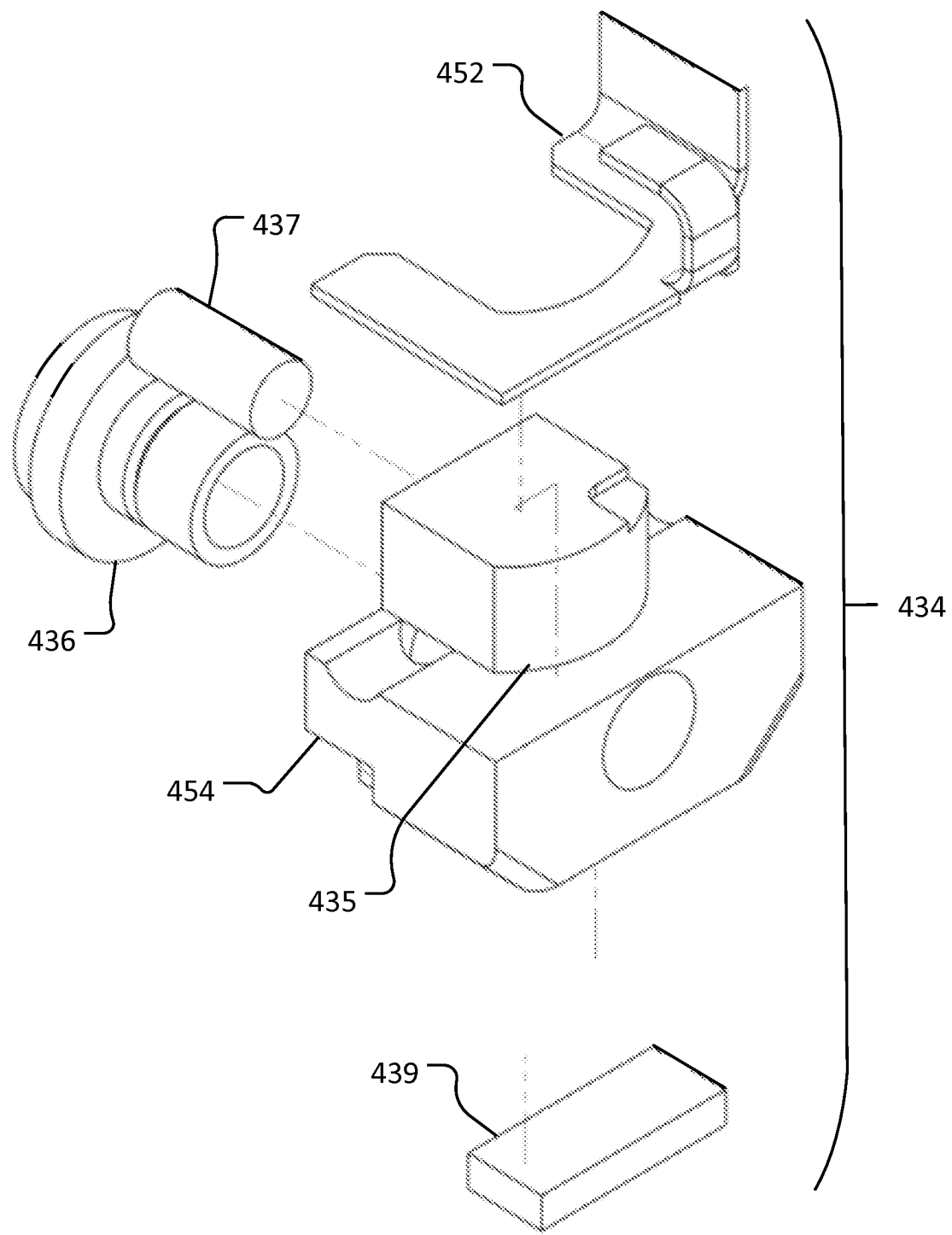
FIG. 7 is a perspective exploded view of a slider portion of the actuation unit of FIG. 6.

Referring also to FIG. 7, an example of the slider unit 434 is shown in an exploded perspective view for greater visibility of the slider unit's components. The slider unit 434 includes a curved member 435, a threaded collar 436, a spring wire retention magnet 437, a slider unit retention magnet 439, a spring wire attachment member 452, and a slider body 454. The threaded collar 436 and the curved member 435 are affixed to the slider body 454. The spring wire retention magnet 437 is affixed to the curved member 435. The spring wire attachment member 452 is engaged with the curved member 435 and the slider body 454. The slider unit retention magnet 439 is affixed to the slider guidance member 438 and magnetically couples with the slider body 454.

The curved member 435 has a contoured lateral face with which the spring wire 440 (refer to FIG. 5) makes contact. As the curved member 435 linearly translates back and forth within the slider guidance member 438, the contact area between the spring wire 440 and the contoured lateral face of the curved member 435 positionally adjusts. That arrangement converts the linear motion of the curved member 435 into a smooth pivoting motion of the spring wire 440 (with the shaft 420 acting as the pivot point).

The spring wire retention magnet 437 attracts the spring wire 440 so that the spring wire 440 remains in contact with the contoured lateral face of the curved member 435 while the back and forth motion of the slider unit 434 takes place. Additionally, in some embodiments the spring wire retention magnet 437 is used in conjunction with a Hall effect sensor mounted on the PCB assembly 470 (refer to FIG. 5) so that the position of the slider unit 434 can be electronically monitored.

The threaded collar 436 has internal threads that are complementary with the external threads of the drive shaft 433 of the motor 432. Accordingly, the threaded collar 436, being constrained from rotating because of engagement with the slider body 454, linearly translates along the length of the drive shaft 433 of the motor 432 as the drive shaft 433 turns. As the threaded collar 436 linearly translates, the slider body 454 and the curved member 435 also linearly translate (because the threaded collar 436 is affixed to the slider body 454). The slider unit retention magnet 439, being affixed to the slider guidance member 438 and magnetically coupled with the slider body 454, serves to precisely maintain the slider body 454 in a close running relationship with the slider guidance member 438 as the slider body 454 translates back and forth in relation to the slider guidance member 438.

The spring wire attachment member 452, which is coupled with the slider body 454, serves to mechanically engage the spring wire 440 (refer to FIG. 5) with the slider unit 434. The spring wire attachment member 452 thereby facilitates a mechanical connection between the spring wire 440 and the slider unit 434 (in addition to the aforementioned magnetic coupling between the spring wire 440 and the spring wire retention magnet 437). Moreover, in some embodiments the spring wire attachment member 452 includes physical features that are used for travel or end-of-travel detection of the slider unit 434. For example, in some embodiments the spring wire attachment member 452 includes one or more projections that are detectable by sensor(s) mounted on the PCB assembly 470. Photo-sensors, proximity sensors, mechanical sensors, and the like, can be used to detect the position of the spring wire attachment member 452 in that fashion.

Figure 8:
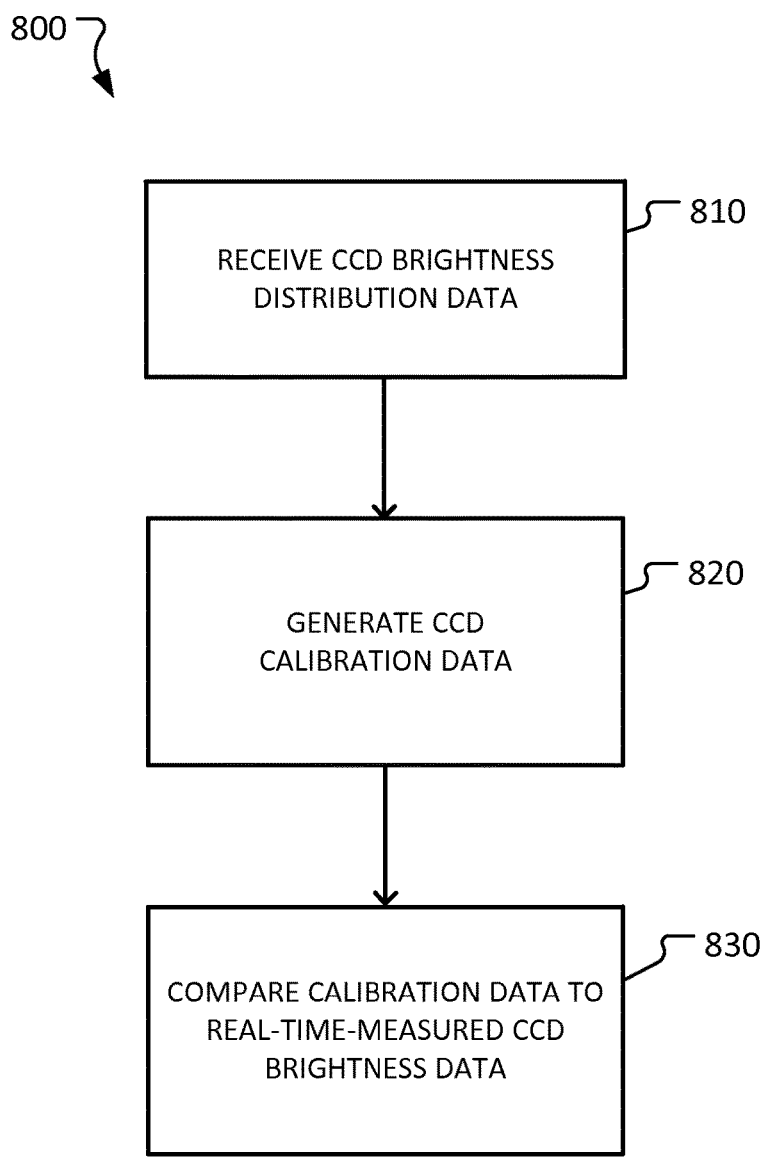
FIG. 8 is a flowchart of an example CCD evaluation process that can be used in conjunction with the thromboelastometry system of FIG. 1.

Referring to FIG. 8, in some embodiments one or more processors of the thromboelastometry system 100 (refer to FIG. 1) is configured to perform a CCD evaluation process 800. In particular embodiments, such a CCD evaluation process 800 can be implemented in one or more processors of an individual AD-module (e.g., in one or more processors of PCB assembly 470 of example AD-module 400; refer to FIGS. 4 and 5). In some such embodiments, each individual measurement module of a thromboelastometry system 100 can include one or more processors that are configured to perform the CCD evaluation process 800. Using the CCD evaluation process 800, thromboelastometry measurement inaccuracies can be reduced or eliminated in some cases. In result, the consistency of the performance (e.g., precision and accuracy) of the thromboelastometry system 100 can be enhanced.

At step 810, one or more processors of the thromboelastometry system or AD-module receives CCD brightness distribution data. In some embodiments, multiple pixels of the CCD of an AD-module are activated using a light source (e.g., LED 450 of the example AD-module 400; refer to FIG. 5). The resulting data generated by the multiple pixels is received by the one or more processors.

At step 820, the one or more processors of the thromboelastometry system or AD-module generates CCD calibration data using the CCD brightness distribution data received in step 810. In some embodiments, this is performed by making an evaluation of the position of a falling or rising edge of the brightness distribution data from the CCD. The falling or rising edge of the brightness distribution data may also be referred to herein as a "flank."

At step 830, the one or more processors of the thromboelastometry system or AD-module compare the calibration data generated in step 820 to real-time-measured CCD brightness data. In some embodiments, the real-time CCD evaluation process of step 830 is run (cycled) repeatedly while the thromboelastometry system is in operation. For example, in some embodiments the cycle time of the ongoing real-time CCD evaluation process 830 is less than about every 200 milliseconds. In some embodiments, the ongoing real-time CCD evaluation process 830 is an optimization process to fit the samples from calibration to the currently measured position of a falling or rising edge of the brightness distribution data (or brightness distribution flank).

Figure 9:
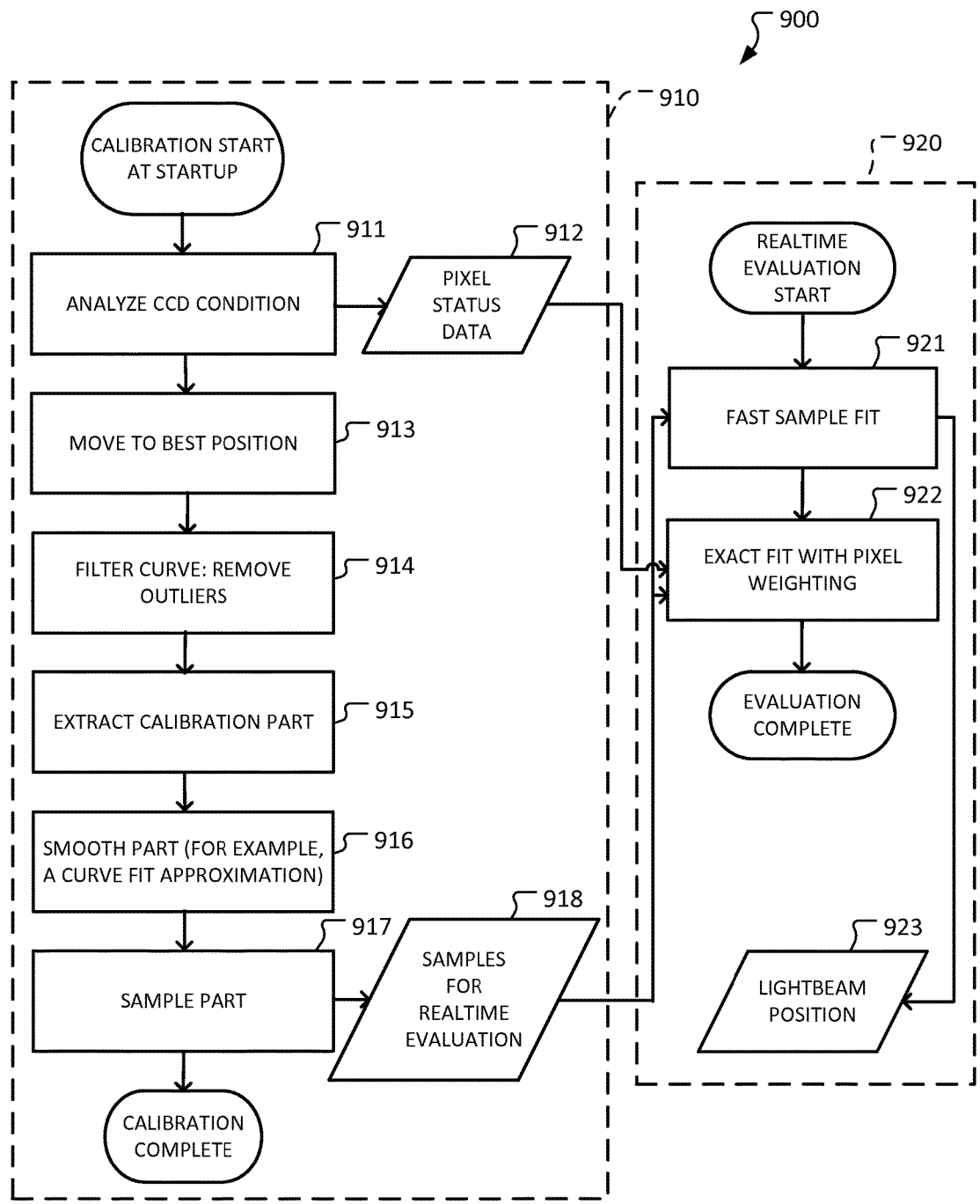
FIG. 9 is a flowchart of another CCD evaluation process that can be used in conjunction with the thromboelastometry system of FIG. 1.

Referring to FIG. 9, in some embodiments one or more processors of the thromboelastometry system 100 (refer to FIG. 1) or AD-module is configured to perform a two-phase CCD evaluation process 900. The two-phase CCD evaluation process 900 includes a startup CCD evaluation process 910 and an ongoing real-time CCD evaluation process 920. Using the two-phase CCD evaluation process 900, thromboelastometry measurement inaccuracies can be reduced or eliminated in some cases. In result, the consistency of the performance (e.g., precision and accuracy) of the individual AD-modules and of the thromboelastometry system 100 as a whole can be enhanced.

In some embodiments, the first stage of the two-phase CCD evaluation process 900 is to generate calibration data in form of samples (data points) to fit on. This is done, starting at step 911, by making an evaluation of the best possible brightness distribution flank at startup of the thromboelastometry system 100. At each test position on the CCD, each light signal distribution is analyzed to decide whether the pixel is OK or not OK. As an example, some pixels of the CCD may be deemed to be not OK due to performance deficiencies caused by contamination on the CCD.

In some embodiments, the condition of the CCD pixels are analyzed by running a moving binomial average over the whole light distribution curve and comparing the resulting values to the measured data. For each pixel, if the difference between the moving binomial average over the whole distribution curve and the pixel's measured value is greater than a threshold value, in some embodiments the pixel is deemed to be not OK. Conversely, if the difference between the moving binomial average over the whole distribution curve and the pixel's measured value is less than a threshold value, the pixel is deemed to be OK.

In step 912, data regarding each pixel is stored in a buffer. That is, because the whole CCD is analyzed in step 911, a map of the disrupted pixels can be calculated by storing the position of all disrupted pixels in a buffer. The data is also used as an input to the ongoing real-time CCD evaluation process 920.

In step 913, the position of the CCD with the least concentration of not OK pixels is determined as the best position to calibrate the CCD evaluation algorithm at. The mirror on the shaft (refer to FIG. 4) is then rotationally positioned so that the LED light reflecting from the mirror is directed to the best position on the CCD.

In step 914, the measured brightness distribution curve at the best position is then filtered to remove outlier errors of the measured brightness distribution curve at the best position. In some embodiments, a filtering process is applied to linearly approximate outlier parts of the brightness distribution curve. This stage is configured to resolve problems caused, for example, by any dirt that shades parts of the CCD. These dirty parts are mostly noticeable as wide and distinct areas of significantly less illumination than usual (outlier errors). In some embodiments, this step uses an algorithm that includes two stages. The first stage is to sample the curve using a fixed step width and looking for unnatural outliers to be corrected. The second stage takes the start point of the outlier and searches for the end of the outlier. It does so by approximating a slope of the brightness distribution curve. The algorithm assumes that the closest OK point is in the area of the extended line of this slope. Looking at the shape of a typical CCD brightness distribution curve and the resulting errors from dirt on the CCD, outliers should only increase point values. This algorithm has a low memory footprint and runs fast in comparison to some more complicated filter kernels and FFT approaches.

In step 915, from the filtered data of step 914, a part of the right falling or rising edge of the brightness distribution data (flank) is extracted. The algorithm is designed to perform a robust detection of the right edge of the outlier filtered brightness distribution given.

In some embodiments, starting from the minimum, the search algorithm is designed to find the latest possible occurrence of a good match to the searched value. Because the brightness distribution data curve is rising, the latest possible occurrence has a high probability of being the wanted position. This custom made algorithm is very fast and reliable with low memory footprint.

In step 916, the extracted brightness distribution flank is then smoothed and sampled. In some embodiments, this is done by applying very little noise to the flank and approximating the result with a curve fit model. Cubic B-splines with sufficient interpolation points can approximate a non-linear curve very well and hence are superior to typical polynomial or linear interpolation that show only good performance if the curve has the right shape.

In steps 917 and 918, samples with fixed step width are extracted as the final calibration step and stored in a buffer. This substantially reduces the memory footprint and speeds up the real-time evaluation, since less comparison operations need to be done.

The startup CCD evaluation process 910 is complete once the buffer containing the positions of the not OK pixels (step 912) and the buffer containing the samples for the real time light beam position evaluation (step 918) are appropriately populated.

The ongoing real-time CCD evaluation process 920 is run (cycled) repeatedly while the thromboelastometry system 100 is in operation. For example, in some embodiments the cycle time of the ongoing real-time CCD evaluation process 920 is about every 50 milliseconds. The ongoing real-time CCD evaluation process 920 is an optimization process to fit the samples from calibration to the currently measured brightness distribution flank.

In step 921, the samples from step 918 are fit in comparison to a target position by an interval based algorithm. The algorithm evaluates the samples in the middle of an interval, which contains the possible target positions on the left side. In some embodiments, the first interval (space) is the whole CCD pixel range. The algorithm then decides if the wanted position is on right or left side of the desired position (which is possible because the brightness distribution is monotone). That is, if any pixel to the right of the middle is bigger, a new right border is determined. The current evaluated position now acts as the new right or left border of the new interval which halves the searched CCD pixel range. This scheme is repeatedly executed until the interval (space) has a length of one which means the destination is reached. This first fast fit algorithm greatly reduces the overall time needed to fit the samples to the measured curve. The algorithm only needs about 10 iterations to find the target position within about 10 pixel accuracy. The algorithm is superior in terms of speed in comparison to the more common least average approach used after this fast fit.

In step 922, a precise weighted convergence to fit the samples as good as possible is performed. This is done by calculating the average of the absolute distances between all samples and their counterparts in the brightness distribution curve. Since for every pixel, information about their status (OK or not OK) is in the memory, one can ignore samples that compare to not OK pixels. This greatly enhances robustness in comparison to a typical approach without ignoring known bad pixels.

In step 923, the location of the samples on the X-Axis (CCD Pixel Position, buffer position) of the light beam position is determined and sent to software.

Figure 10:
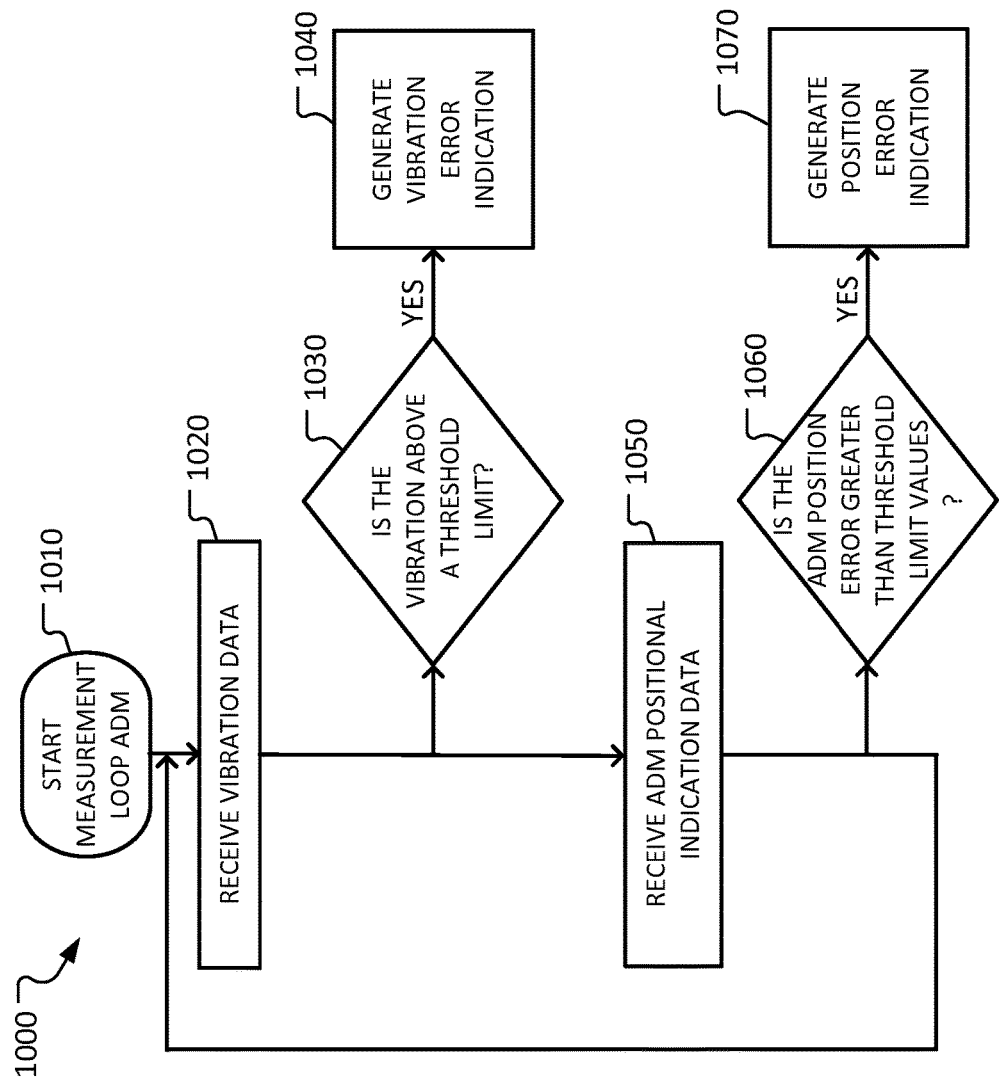
FIG. 10 is a flowchart of a thromboelastometry measurement quality control process that can be used in conjunction with the thromboelastometry system of FIG. 1.

Referring to FIG. 10, an AD-module error detection process 1000 is a loop process that can be performed by a processor of a thromboelastometry measurement system. The AD-module error detection process 1000 can be performed to evaluate parameters that may be indicative of thromboelastometry actuation and detection system error causes.

At step 1010, the AD-module error detection process 1000 begins. The AD-module error detection process 1000 can be performed in parallel with a thromboelastometry measurement process.

At step 1020, a processor of the thromboelastometry measurement system receives data that pertains to a detected amount of vibration that may affect the accuracy or precision of thromboelastometry measurement data from an AD-module. In some embodiments, the vibration is measured via a ball-based sensor that is a component of the AD-module (e.g., located on a PCB within the AD-module housing). In some embodiments, other types of sensors are used for vibration detection, such as one or more accelerometers, piezoelectric sensors, displacement sensors, velocity sensors, and the like.

At step 1030, the processor compares the received vibration data to one or more threshold values. If the received vibration data is greater than the threshold values, the processor generates a vibration-related error indication in step 1040.

At step 1050, a processor of the thromboelastometry measurement system receives data that pertains to a detected position of moving components of an AD-module that may affect the accuracy or precision of thromboelastometry measurement data from the AD-module. For example, the positional indication data may include, but is not limited to, end-of-travel data, rotational position data, linear translation position data, and the like, and combinations thereof. In some embodiments, an end-of-travel switch that is a component of the AD-module (e.g., located on a PCB within the AD-module housing) is used to detect the absolute position of the AD-module actuation unit. In some embodiments, the end-of-travel switch is in form of a photo optic sensor, or a proximity sensor, limit switch, and the like. In some embodiments, a Hall effect sensor that is a component of the AD-module (e.g., located on a PCB within the AD-module housing) is used to generate positional indication data. Other types of sensors that provide positional indication data may also be utilized.

At step 1060, the processor compares the received data that pertains to a detected position of moving components of an AD-module to one or more threshold values. If the received positional data is greater than the threshold values, the processor generates a position error indication in step 1070. The process 1000 loops back to step 1020 and repeats the process 1000.

Figure 11:
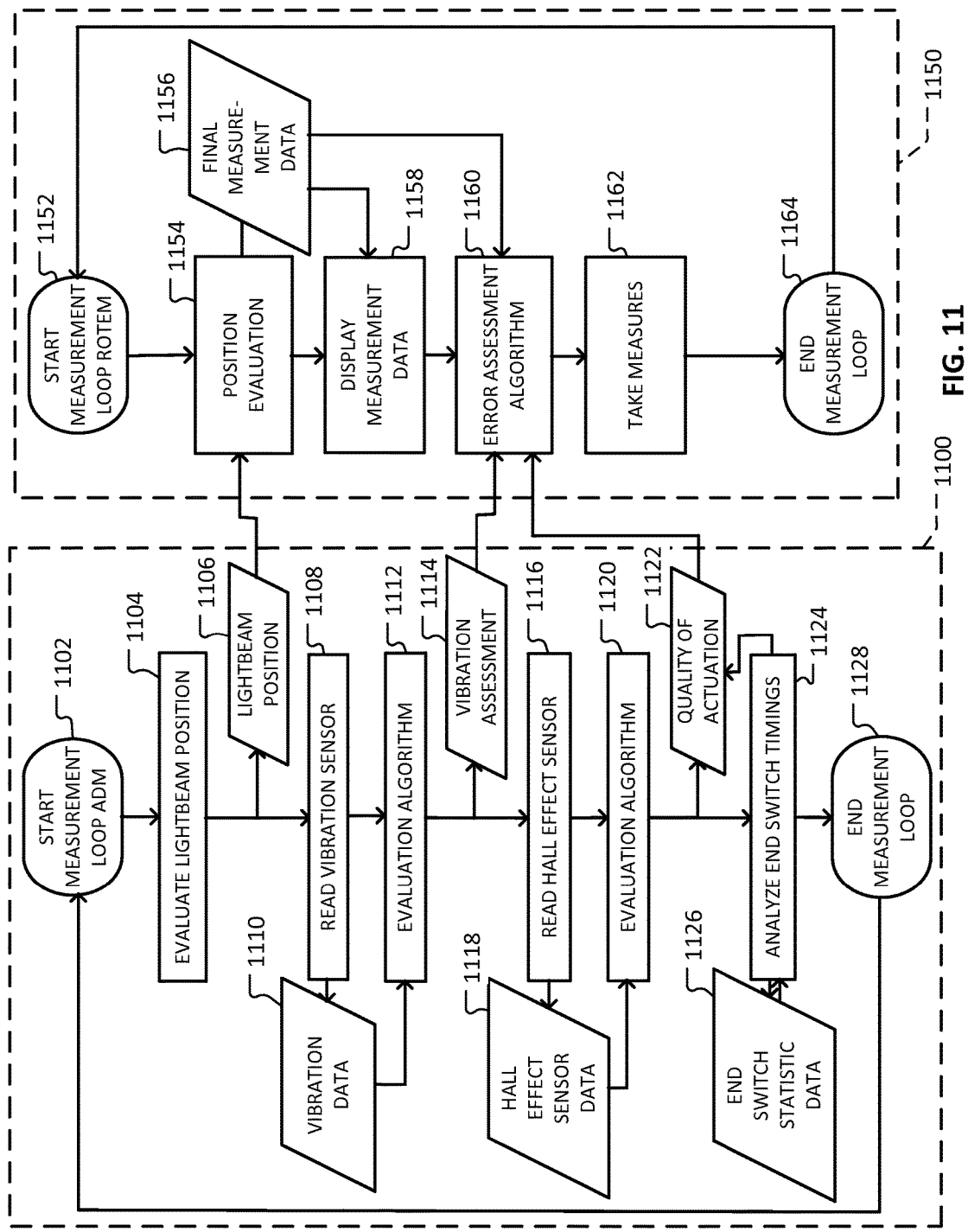
FIG. 11 is a flowchart of another thromboelastometry measurement quality control process that can be used in conjunction with the thromboelastometry system of FIG. 1.

Referring to FIG. 11, a process flowchart describes an AD-module measurement loop 1100 and a thromboelastometry measurement and evaluation loop 1150 in substantial detail. The processes 1100 and 1150 include steps for supervising the operations of a thromboelastometry system 100 (refer to FIG. 1) to enhance error detection and the accuracy of the thromboelastometry system.

During thromboelastometry measurement, key aspects are supervised and evaluated in real-time using processes 1100 and 1150. For example, vibrations that might distort the measurement signal are supervised and evaluated. Also, the movement quality of the rotary thromboelastometry actuation and detection system is supervised and evaluated with a Hall effect sensor. In addition, the movement precision of the rotary thromboelastometry actuation and detection system is supervised and evaluated using one or more end-of-travel sensors. Further, the quality of the measurement signal is evaluated. The vibration, movement quality, and movement precision, in combination with the light beam position, allow the processor of the thromboelastometry system to determine the current quality of the measurement signal, analyze the cause of distortions, and take responsive measures.

In some embodiments, the AD-module measurement loop 1100 is executed about every 50 milliseconds. In particular embodiments, the AD-module measurement loop 1100 is part of the normal measurement routine on the AD-module.

Steps 1104 and 1106 pertain to the position of the LED light beam of the AD-module. For example, in some embodiments the light beam position is detected and evaluated.

Steps 1108 to 1114 pertain to the evaluation of the vibration. In some embodiments, the vibration is measured via a ball-based sensor that is a component of the AD-module (e.g., located on a PCB within the AD-module housing). In some embodiments, other types of sensors are used for vibration detection, such as one or more accelerometers, piezoelectric sensors, displacement sensors, velocity sensors, and the like. The resulting data that needs to be evaluated are vibration events over time. A typical evaluation algorithm could be a limit only allowing a certain amount of vibration events over a certain amount of time. If the limit is exceeded, an error message is sent to the processor running the thromboelastometry measurement software.

Steps 1116 to 1120 include the evaluation of the rotary thromboelastometry actuation and detection system by supervision with a Hall effect sensor that is a component of the AD-module (e.g., located on a PCB within the AD-module housing). The measured data provides a characterization of the actual movement of the system. In some embodiments, an evaluation algorithm could be run to compare the measured movement with the theoretical movement the rotary thromboelastometry actuation and detection system should execute. For example, a sum of absolute/squared difference between theory and reality are suitable algorithms when optimized properly. If a threshold amount of differences are detected, an error message is sent to the processor running the thromboelastometry measurement software (at step 1122).

Steps 1124 and 1126 include the evaluation of the absolute movement position of the rotary thromboelastometry actuation and detection system. An end switch that is a component of the AD-module (e.g., located on a PCB within the AD-module housing) is used to detect the absolute position of the actuation unit with sub step (stepper motor) precision. In some embodiments, the end switch is in form of a photo optic sensor, or a proximity sensor, limit switch, and the like. The gathered statistical data of the deviation from the optimal position is used to determine if the actuation is operating as expected. If the actual position is differing enough from the target position for a threshold amount of time, an error message is sent to the processor running the thromboelastometry measurement software (at step 1122).

At step 1122, the data gathered regarding the actuation quality from steps 1116 through 1126 allows a complete evaluation of the motion quality of the rotary thromboelastometry actuation and detection system. In some embodiments, the evaluation is attainable at low cost and small space in comparison, for example, to using an extra encoder for monitoring the stepper motor.

Turning now to a description of the thromboelastometry measurement and evaluation loop 1150. Steps 1154 through 1158 pertain to the thromboelastometry measurement process as performed by the processor running the thromboelastometry measurement software.

Steps 1160 and 1162 describe the evaluation of the errors sent by the AD-module from process 1100. After the position is evaluated, the additional errors sent by the AD-module can be used to interpret the currently known errors by the processor running the thromboelastometry measurement software. The error type and frequency are evaluated by the software, and error messages are shown to the user if they are significant enough in frequency or if they are critical enough. In some embodiments, the AD-module errors can be correlated to measurement errors by the processor running the thromboelastometry measurement software, delivering additional information on what caused the errors and assisting further improvements on hardware, electronics, and firmware.

A number of embodiments of the invention have been described. Nevertheless, it will be understood that various modifications may be made without departing from the scope of the invention. Accordingly, other embodiments are within the scope of the following claims.

What is claimed is:

1. A control console for measuring coagulation characteristics of a blood sample, the control console comprising:
    a control unit housing;
    a user interface coupled to the control unit housing for displaying coagulation characteristics of a blood sample; and
    a plurality of individual thromboelastometry measurement modules housed in the control unit housing, each measurement module of the plurality of individual thromboelastometry measurement modules including a shaft configured to receive a probe for testing the blood sample using a probe and cup arrangement,
    wherein each individual measurement module of the plurality of individual thromboelastometry measurement modules includes a dedicated actuation unit comprising a magnet that magnetically couples a spring wire to a slider unit and is configured to provide linear translation of a slider unit that drives rotation of a respective shaft of the individual measurement module independently from rotation of shafts of all other individual measurement modules of the plurality of individual thromboelastometry measurement modules.

2. The control console of claim 1, wherein the actuation unit comprises a stepper motor, wherein the stepper motor includes a threaded driveshaft, wherein the actuation unit further comprises the slider unit, and wherein the slider unit comprises a threaded collar that is threadably engaged with the threaded drive shaft such that the stepper motor can drive the slider unit to translate linearly.

3. The control console of claim 2, wherein the actuation unit further comprises a spring wire, and wherein a linear translation of the slider unit causes a pivoting of the shaft because of the spring wire extending between the slider unit and the shaft.

4. The control console of claim 1, wherein the spring wire is magnetically attracted to a curved surface of the slider unit.

5. The control console of claim 1, wherein each individual measurement module of the plurality of individual thromboelastometry measurement modules includes an evaluation unit for evaluating a charge-coupled device (CCD) component, the evaluation unit being configured to (i) receive brightness distribution data from the CCD, (ii) generate CCD calibration data based on the brightness distribution data, and (iii) compare the CCD calibration data to real-time-measured CCD brightness distribution data.

* * * * *